(12) United States Patent
Hammarback (10) Patent No.: US 9,750,834 B1
(45) Date of Patent: Sep. 5, 2017

(54) WATER TREATMENT DISPENSING APPARATUS

(71) Applicant: Barry J Hammarback, Riverfalls, WI (US)

(72) Inventor: Barry J Hammarback, Riverfalls, WI (US)

(73) Assignee: Crosstex International, Inc., Hauppauge, NY (US)

( * ) Notice: Subject to any disclaimer, the term of this patent is extended or adjusted under 35 U.S.C. 154(b) by 676 days.

(21) Appl. No.: 13/730,808

(22) Filed: Dec. 28, 2012

Related U.S. Application Data (60) Provisional application No. 61/631,207, filed on Dec. 29, 2011.

(51) Int. Cl.
*A61L 2/16* (2006.01)
*B01D 24/00* (2006.01)
*B01D 27/08* (2006.01)
*C02F 9/00* (2006.01)
*A61C 1/00* (2006.01)
(Continued)

(52) U.S. Cl.
CPC .............. *A61L 2/16* (2013.01); *A61C 1/0061* (2013.01); *A61L 2/23* (2013.01); *B01D 24/008* (2013.01); *B01D 27/08* (2013.01); *B05B 7/00* (2013.01); *B05B 7/0025* (2013.01); *C02F 9/005* (2013.01); *A61C 1/0076* (2013.01); *A61L 2/238* (2013.01); *A61L 2202/122* (2013.01); *A61L 2209/133* (2013.01); *B01D 24/007* (2013.01); *B01D 2201/291* (2013.01); *C02F 1/50* (2013.01);
(Continued)

(58) Field of Classification Search
CPC ...... C02F 9/00; C02F 9/005; C02F 2301/066; C02F 1/74; C02F 1/50; C02F 1/505; C02F 1/687; C02F 1/688; C02F 2201/006; A61C 1/0076; A61C 1/0061; A61C 1/052; A61L 2/16; A61L 2/26; A61L 2/238; A61L 2202/122; A61L 2209/133; A61L 2/23; B01D 2201/202; B01D 27/00; B01D 46/001; B01D 2201/29; B01D 2201/295; B01D 2201/304; B01D 2201/4061; B01D 24/04; B01D 24/165; B01D 24/08; B01D 24/183; B01D 24/263; B01D 36/02; B01D 33/41; B01D 33/42; B01D 2201/291; B01D 24/007; B01D 24/008; B01D 4/08; B01D 24/12; B01D 24/18; B01D 27/08; F16L 13/0236; F16L 37/10; B05B 7/0025; B05B 7/00
USPC ................ D23/209, 207, 225; D24/176, 177
See application file for complete search history.

(56) References Cited

U.S. PATENT DOCUMENTS

1,637,095 A * 7/1927 Walters .................... F16L 37/10
285/254
3,490,580 A * 1/1970 Robinson .................. A61L 2/12
206/440
(Continued)

*Primary Examiner* — Lucas Stelling
*Assistant Examiner* — Angel Olivera
(74) *Attorney, Agent, or Firm* — Sorell, Lenna & Schmidt LLP; William D. Schmidt, Esq.

(57) ABSTRACT

A water treatment dispensing apparatus has a container for holding water from a water supply and a water disinfectant cartridge located within the container. A housing attached to the container and connected to the cartridge directs water from the cartridge to a remote location, such as a dental instrument. An air pressure device supplies water under pressure to the container to force water to flow through the cartridge and to the remote location.

48 Claims, 11 Drawing Sheets

(51) Int. Cl.
  *B05B 7/00* (2006.01)
  *A61L 2/23* (2006.01)
  *C02F 1/50* (2006.01)
  *A61L 2/238* (2006.01)

(52) U.S. Cl.
  CPC ........ *C02F 1/505* (2013.01); *C02F 2201/006* (2013.01)

(56) References Cited

U.S. PATENT DOCUMENTS

| | | |
|---|---|---|
| 3,788,476 A * | 1/1974 | Othmer .................. 210/194 |
| 4,238,477 A * | 12/1980 | Lambert et al. ............ 521/31 |
| 5,073,382 A * | 12/1991 | Antelman .............. 424/604 |
| 5,223,149 A | 6/1993 | Antelman |
| 5,230,624 A | 7/1993 | Wolf et al. |
| D351,892 S | 10/1994 | Wolf et al. |
| 5,370,534 A | 12/1994 | Wolf et al. |
| 5,401,399 A | 3/1995 | Magnusson et al. |
| 5,556,279 A | 9/1996 | Wolf et al. |
| 5,882,507 A | 3/1999 | Tanner et al. |
| 6,254,894 B1 | 7/2001 | Denkewicz et al. |
| 6,325,929 B1 | 12/2001 | Bassett |
| 6,562,241 B1 * | 5/2003 | Gritton et al. ............ 210/721 |
| 7,250,111 B2 | 7/2007 | Doxey et al. |
| 7,329,385 B1 * | 2/2008 | Radicone et al. ............ 422/4 |
| 7,491,330 B2 | 2/2009 | Harvey |
| 7,704,399 B2 | 4/2010 | Condit |
| 8,252,185 B2 | 8/2012 | Rajan et al. |
| 2006/0208397 A1 * | 9/2006 | Ichikawa ............ B28B 3/206 264/631 |

* cited by examiner

WATER TREATMENT DISPENSING APPARATUS

CROSS REFERENCE TO RELATED APPLICATION

This application claims the priority benefit of U.S. Provisional Application Ser. No. 61/631,207 filed Dec. 29, 2011.

FIELD OF THE INVENTION

The invention relates to the art of water treatment and purification technology. The particular water treatment of the invention concerns a water purification apparatus for a dental water system. The apparatus includes a water purification cartridge having disinfectant particulate substances and resins that neutralize microorganisms, bacteria, viruses, protozoa and pathogens.

BACKGROUND OF THE INVENTION

Human and animal populations, agricultural and industrial development and natural disasters have reduced the supply of potable water. Pollutants that pose a threat to humans and animals are pathogens including bacteria and viruses along with organic and inorganic contaminants. Water can contain suspended materials, dissolved solids, and bacteriological contaminants. Domestic water systems are increasingly being contaminated with pollutants that effect human and animal health.

Medical and dental uses of water require a supply of water that does not contain organic, inorganic and pathogenic contaminants. Conventional tap water must be treated to remove organic and inorganic materials and destroy pathogenic contaminants, such as bacteria and viruses that are detrimental to humans. Dental instruments used in dental treatment theaters and clinics utilize coolant and rinse water. The water supply can be tap water or bottled water. The water supply can be contaminated with organic and inorganic materials pathogenic microorganisms. Contaminated water can cause infection in dental patients and cross-infection between dental patients. Dental treatment includes subgingival invasion of the mucosa therefore providing direct access to the patient's vascular system. It is prudent to use microbiologically treated water for use with dental instruments in the dental treatment theater.

Water purification cartridges have been used with dental instruments to provide the dental instruments with clean and disinfected water. The cartridges are located in the water lines connected to the dental instruments. The cartridges have water purification resins containing polyiodide that neutralizes and kills disease-causing bacteria, viruses and protozoa. The water discharged by the dental instrument contains the disinfectant thereby reducing the potential of cross infection between dental patients. Examples of a water purification system for a dental instrument is disclosed by Leo H. Wolf and Mark F. Wolf in U.S. Pat. Nos. 5,230,624; 5,370,534 and 5,556,279.

SUMMARY OF THE INVENTION

The water treatment dispensing apparatus functions to neutralize and destroy the active effectiveness of pathogenic contaminants including water borne bacteria and viruses to provide safe and clean potable water. The apparatus has a container or bottle having an internal chamber for holding water. The container is releasably mounted on a housing to allow the container to be removed from the housing for cleaning and replacement of a cartridge located within the container. A water supply unit is operable to supply water to the housing for discharge into the interior chamber of the container. The water source can be tap water from a municipal water supply or bottled water including distilled or deionized water. An air pressure device operates to supply air under pressure to the housing and internal chamber of the container to subject the water in the internal chamber to air pressure. A cartridge containing a bed of disinfectant material located in the internal chamber has an end member connected to the housing to allow disinfected water to flow out of the cartridge to the housing and from the housing to a desired location. The air pressure in the interior chamber forces the water in the internal chamber of the container to flow through the cartridge. Filters associated with end member sleeves retain the bed of disinfectant material in the internal chamber of the container and remove organic, inorganic and microbiological contaminants from the water flowing into and out of the internal chamber of the cartridge. An air pressure gauge connected to the housing monitors the pressure of the air in the internal chamber of the container.

The cartridge has an elongated tubular body having an internal chamber or lumen accommodating disinfectant material, including multi-valent iodine resin, silver compositions and silver impregnated activated carbon. A first end member releasably mounted on one end of the tubular body has a passage allowing water from the internal chamber of the container to flow into the internal chamber of the tubular body. The first end member includes a sleeve accommodating a filter operative to remove organic and inorganic materials from the water flowing through the filter. The sleeve is releasably mounted on the tubular body to allow the end member to be placed on and removed from the tubular body and to allow the disinfectant material to be placed in the internal chamber of the tubular body. A second end member releasably mounted on the water outlet end of the tubular body is attached to the housing to fix the location of the cartridge in the internal chamber of the container with the cartridge extended into the water in the internal chamber of the container. The second end member includes a sleeve accommodating a filter operative to retain the disinfectant material in the internal chamber of the tubular body.

The water treatment dispensing apparatus including the cartridge containing disinfectant material is usable in medical and dental applications. A flexible conduit or hose is joined to the water inlet of the dynamic dental instrument to supply the instrument with clean and disinfected water. The conduit is easy to install without the need to cut into expensive dental instrument tubing. Iodine containing disinfectant material is an effective destroyer of water borne pathogenic organisms. Other types of disinfectant materials can be used to inhibit and destroy bacteria, viruses and pathogens in water supplied from the cartridge to the dental instrument.

DESCRIPTION OF WATER DISPENSING APPARATUS

Figure 1:
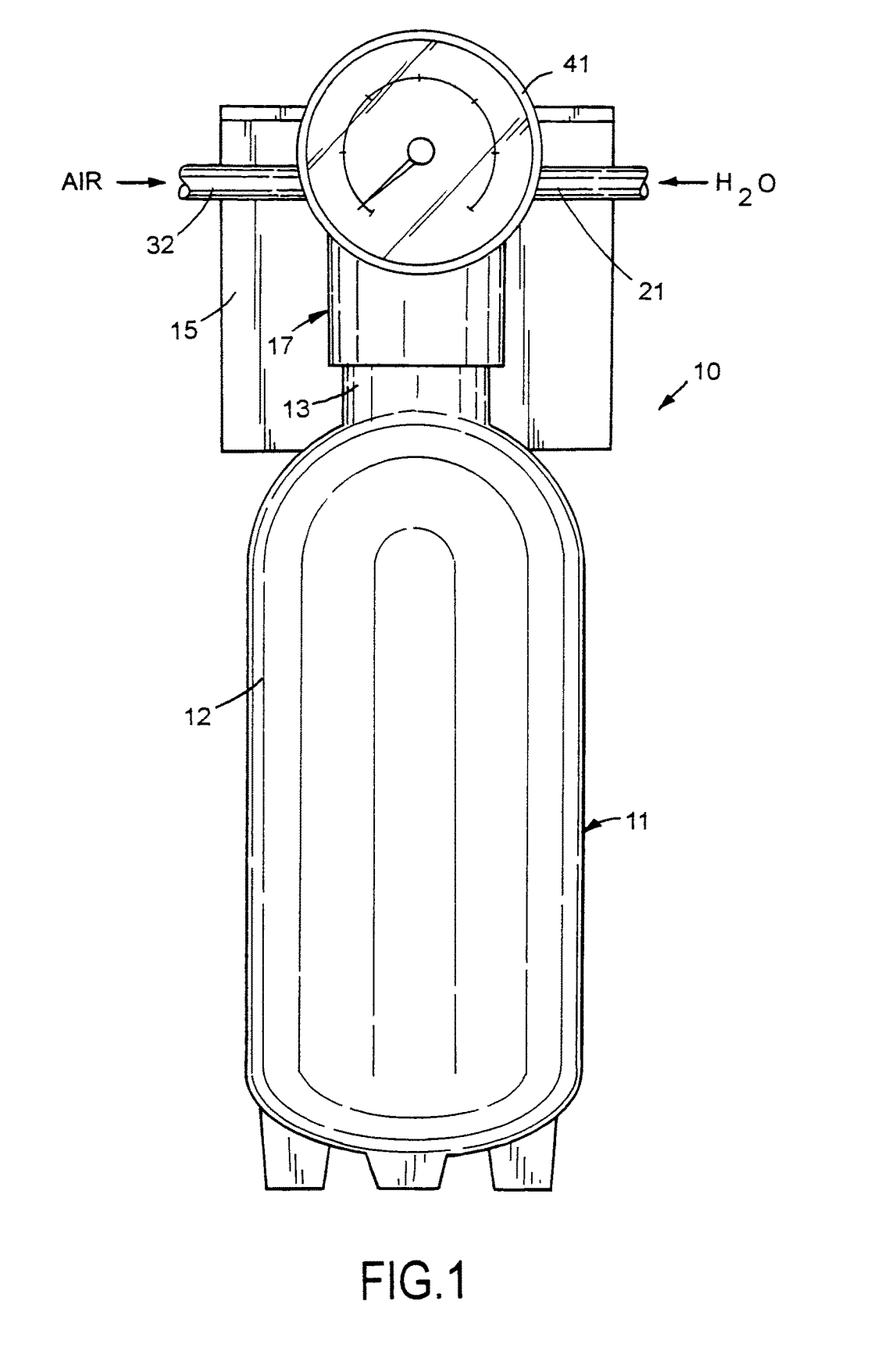
FIG. 1 is a front elevational view of a water treatment dispensing apparatus having a water disinfectant cartridge.
Figure 2:
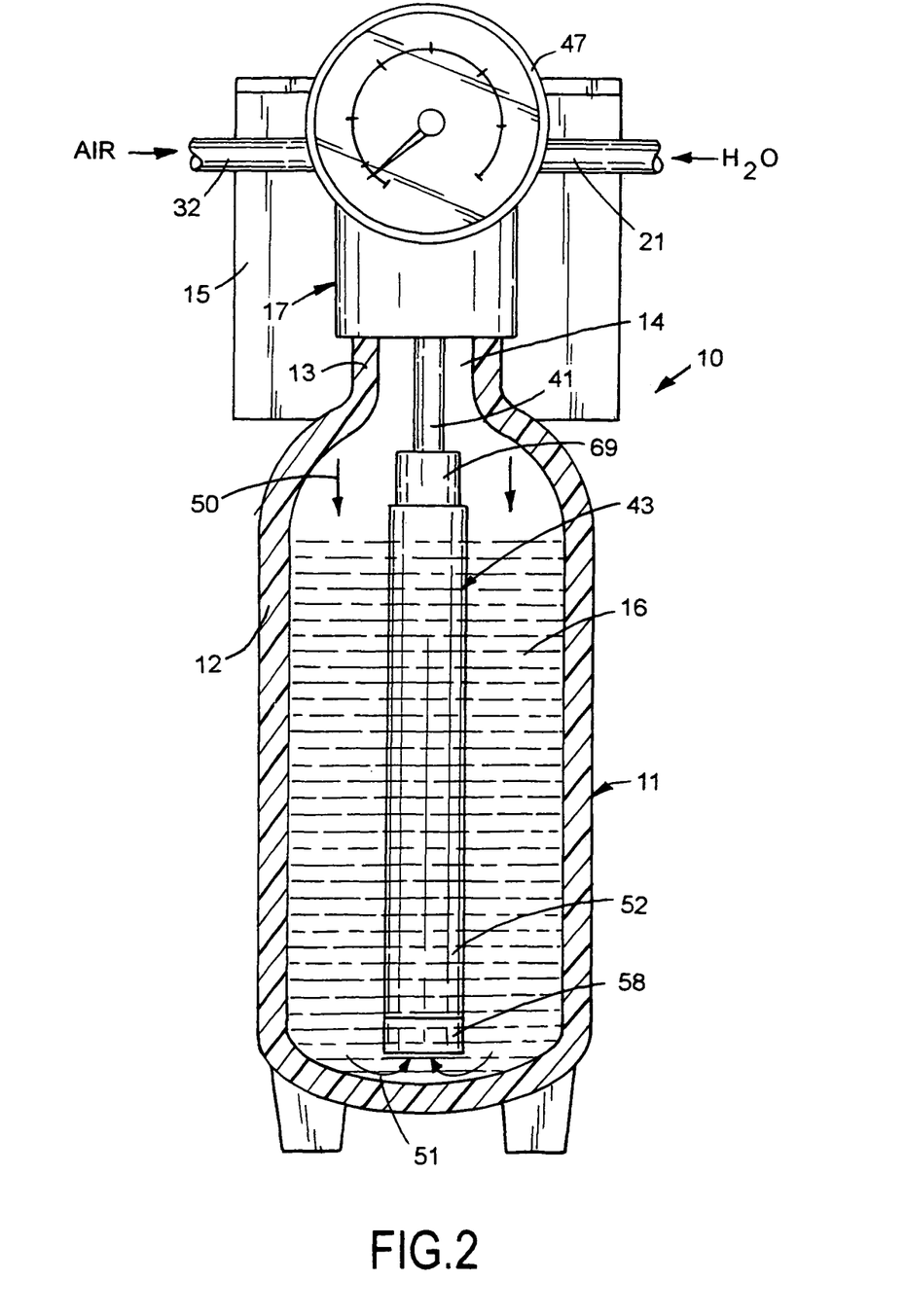
FIG. 2 is a front elevational view partly sectioned of the water treatment dispensing apparatus showing the water disinfectant cartridge.
Figure 3:
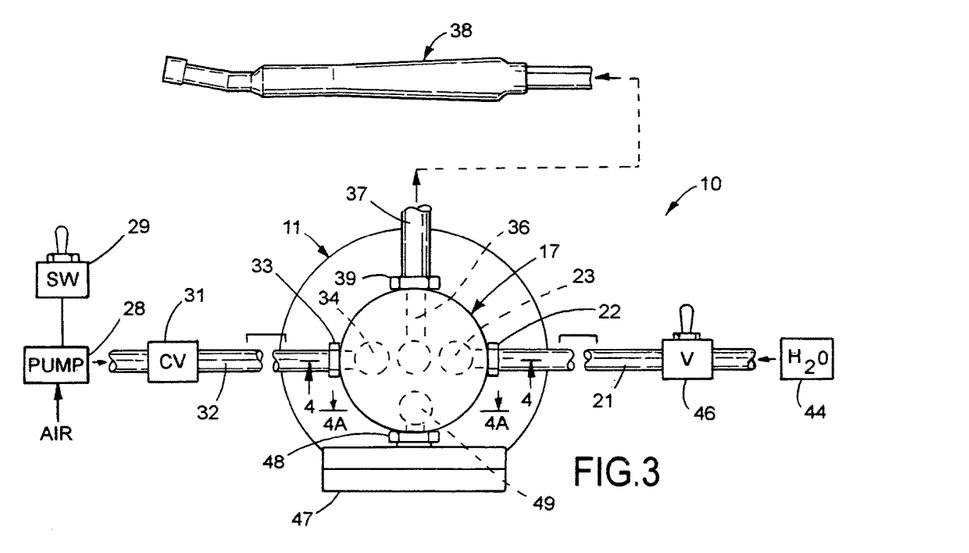
FIG. 3 is a diagram of the top plan view of FIG. 1 employed with a dynamic dental instrument.
Figure 4:
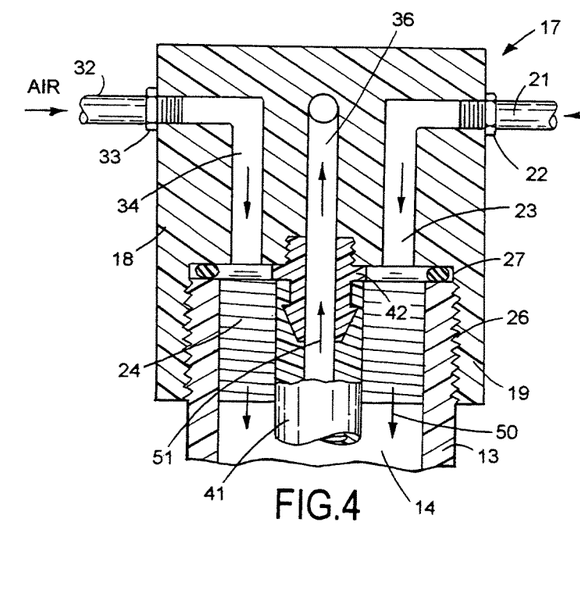
FIG. 4 is an enlarged sectional view taken along line 4-4 of FIG. 3.

A water treatment dispensing apparatus 10, shown in FIGS. 1 and 2, has a container or bottle 11 joined to a housing or cap 17. Container 11 has a cylindrical side wall 12 and a neck 13 surrounding an internal chamber 16. Neck 13 includes a passage 14 open to chamber 16 and the bottom of cap 17. Neck 13 and cap 17 have cooperating threads 26 or releasable connectors that allow container 11 to be turned on and off of cap 17. A bracket 15 retains cap 17 on a support. Other structures can be used to hold cap 17 and container 11 in a fixed position. As shown in FIG. 4, cap 17 has a body 18 joined to a downwardly directed sleeve 19. Body 18 is connected to a tube 21 with a connector 22 for supplying water to a passage 23 in body 18. Passage 23 is open to passage 14 whereby water 20 is dispensed into chamber 16. As shown in FIG. 3, a water supply unit connected to a water supply 44 directs water into tube 21. A valve 46 incorporated in tube 21 is manually operated to regulate the flow of water into chamber 16. Water supply 44 can be ordinary tap water from a municipal water system. Distilled or deionized water in a bottle can be dispensed into chamber 16. Water having a pH level less than 8 and a chlorine level less than 6 is preferred. As shown in FIG. 4, sleeve 19 surrounds a cavity 24 accommodating neck 13 of container 11. Neck 13 and sleeve 19 have cooperating threads 26 that retain container 11 on cap 17. A seal 27, shown as an O-ring, located between the annular end of neck 13 and body 18 prevents air and water leakage from container 11. Container 11 is manually turned to attach container 11 to cap 17 and remove container 11 from cap 17.

Compressed air is supplied to cap 17 with an air supply unit having an air pump 28 driven with an electric motor controlled with a manually operated controller 29. Air is directed to a check valve 31 located in a tube 32. A connector 33 secures tube 32 to body 18 to direct air to a passage 34 in body 18 open to neck passage 14. As shown in FIG. 2, air in chamber 16 applies pressure, shown by arrows 50, on water 20 to force the water to flow into a water purification cartridge 43. The water exit end of cartridge 43 is connected to a tube 41 joined with a connector 42 to body 18 of cap 17. Body 18 has a passage 36 open to tube 41 and a flexible conduit or hose 37 operable to transport water shown by arrow 51 from container 11 to a dental hand instrument 38. A connector 39 joins hose 37 to body 18 of cap 17. Dental instrument 38 shown as a dental hand piece includes an air/water syringe, ultrasonic scaler or other dynamic dental instruments.

Figure 4A:
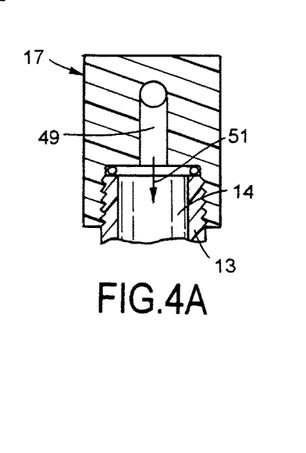
FIG. 4A is a sectional view taken along line 4A-4A of FIG. 3.
Figure 5:
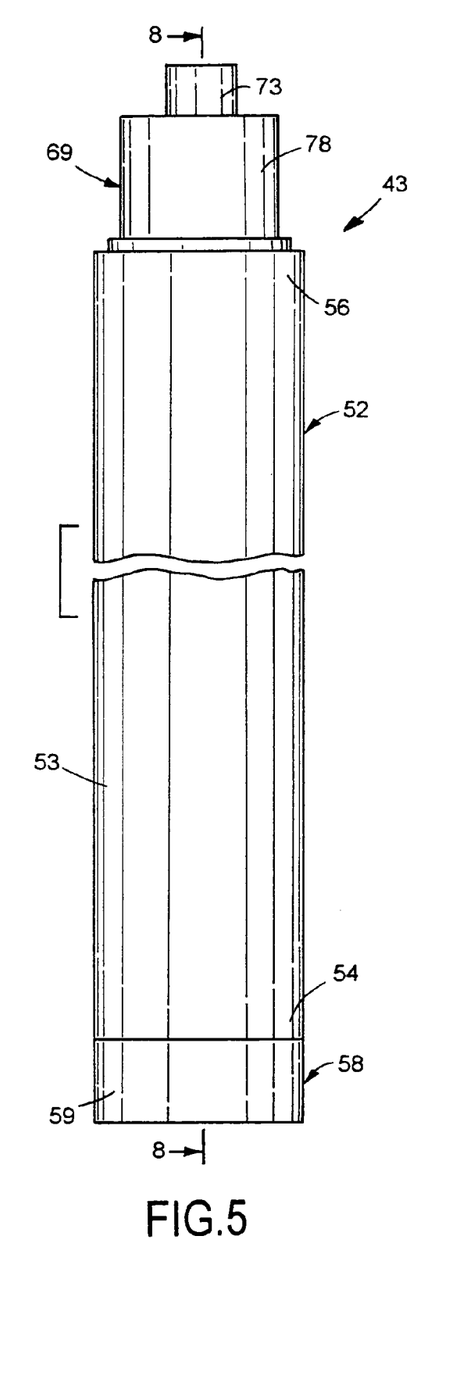
FIG. 5 is an enlarged foreshortened front elevational view of the first embodiment of the water disinfectant cartridge employed in the water treatment dispensing apparatus of FIGS. 1 and 2.
Figure 6:
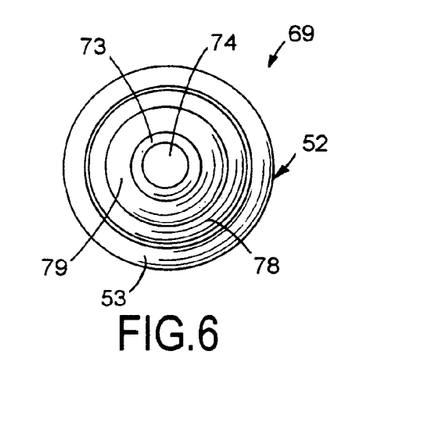
FIG. 6 is a top plan view of FIG. 5.
Figure 7:
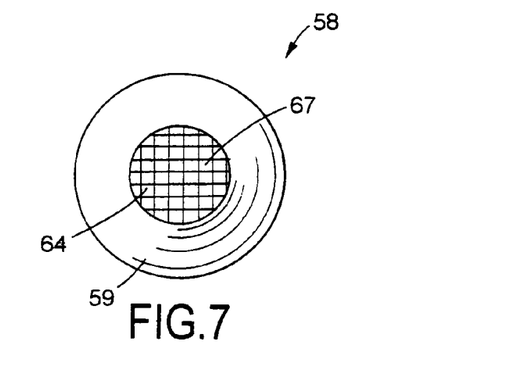
FIG. 7 is a bottom plan view of FIG. 5.

The air pressure in chamber 16 is monitored with an air pressure gauge 47 mounted on body 18 of cap 17 with a connector 48. Gauge 47 has an indicator providing visual information concerning the air pressure in chamber 16. Other types of air pressure gauges or indicators can be used to monitor the air pressure in chamber 16. As shown in FIGS. 3 and 4A, body 18 has a passage 49 connecting air pressure gauge 47 with passage 14 whereby gauge 47 visually displays the air pressure in chamber 16. The air pump 28 is operated to supply air under pressure to chamber 16 at selected air pressure levels.

A first embodiment of cartridge 43, shown in FIGS. 5 to 11, comprises an elongated linear tubular body 52 having a cylindrical side wall 53 including a first inlet end 54 and a second outlet end 56 surrounding an internal chamber 57. Body 52 is a tubular one-piece member of polymeric material, such as rigid polyethylene or like materials that are resistant to build up of organic matter inside the tubular member. Polypropylene and polyvinyl chloride can be used as materials for the tubular member. A first end member 58 attached to inlet end 54 of body 52 allows water from chamber 16 to flow into chamber 57 of body 52. Member 58 has a base 59 joined to a sleeve 61. Body inlet end 54 and sleeve 61 have cooperating threads 63 that allow member 58 to be assembled on and removed from end 54. When base 59 is assembled on end 54, an annular shoulder of base 59 is located in engagement with the annular bottom surface 62 of end 54. Base 59 has an opening 64 in communication with a cavity 66 in base 59 and sleeve 61. A filter 67 located in cavity 66 is used to remove organic, inorganic and foreign materials from the water flowing into chamber 57. Filter 67 is a cylindrical polypropylene member having small porosity such as 5 microns. Other types of filters can be used to remove particulates from the water flowing through member 58 into chamber 57. Filter 67 can be removed from cavity 66 and replaced with another filter. The filter 67 can extend into chamber 57. Filter 67 can include activated charcoal that functions to remove chlorine and chlorine compounds from the water flowing out of the filter into chamber 57.

Figure 8:
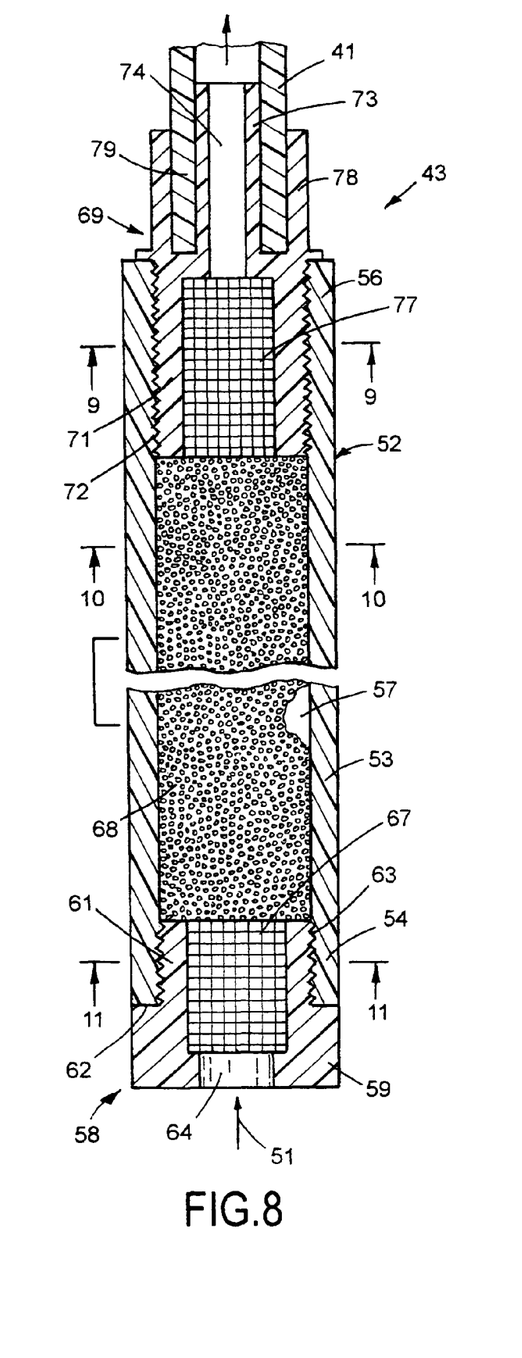
FIG. 8 is a foreshortened sectional view taken along the line 8-8 of FIG. 5.
Figure 9:
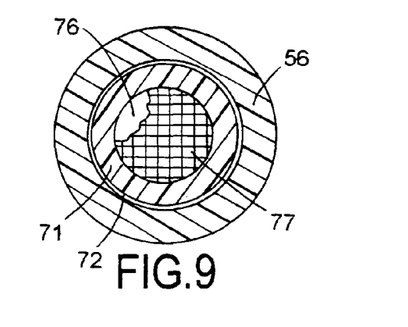
FIG. 9 is a sectional view taken along the line 9-9 of FIG. 8.
Figure 10:
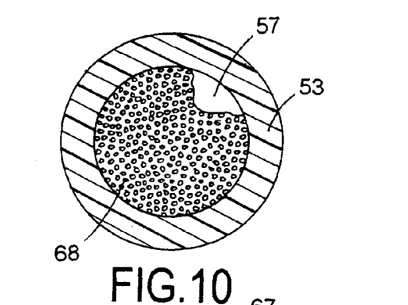
FIG. 10 is a sectional view taken along the line 10-10 of FIG. 8.
Figure 11:
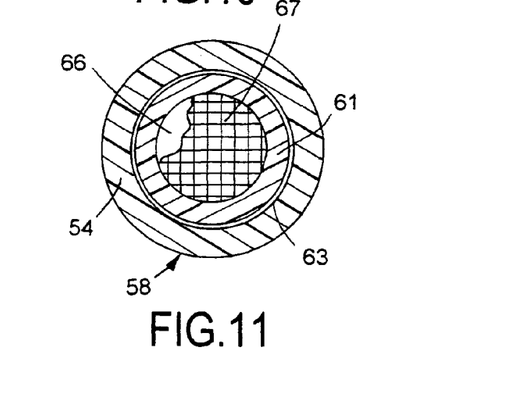
FIG. 11 is a sectional view taken along the line 11-11 of FIG. 8.
Figures 12, 13, 14:
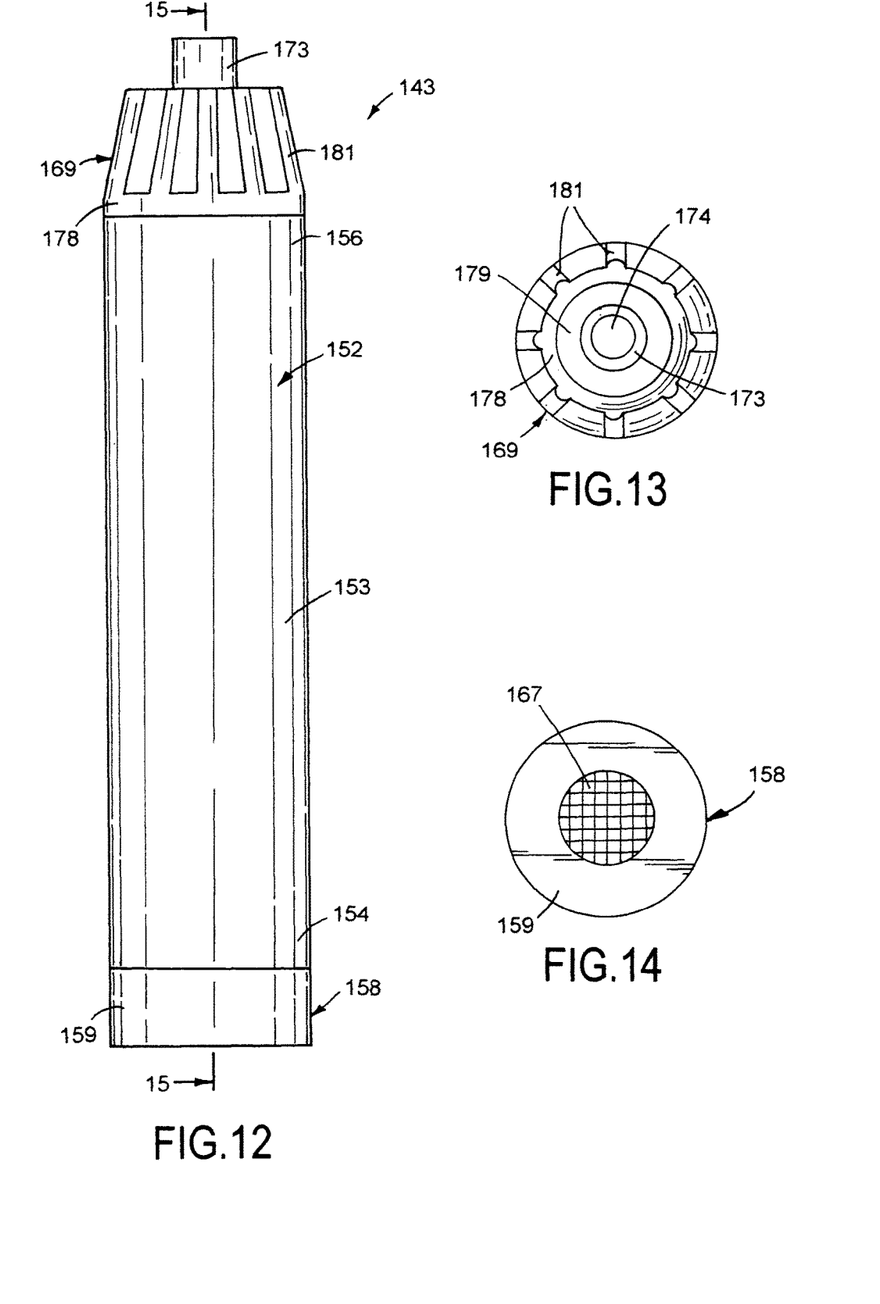
FIG. 12 is an enlarged foreshortened front elevational view of a second embodiment of the water disinfectant cartridge.
FIG. 13 is a top plan view of FIG. 12.
FIG. 14 is a bottom plan view of FIG. 12.
Figures 15, 16, 17, 18:
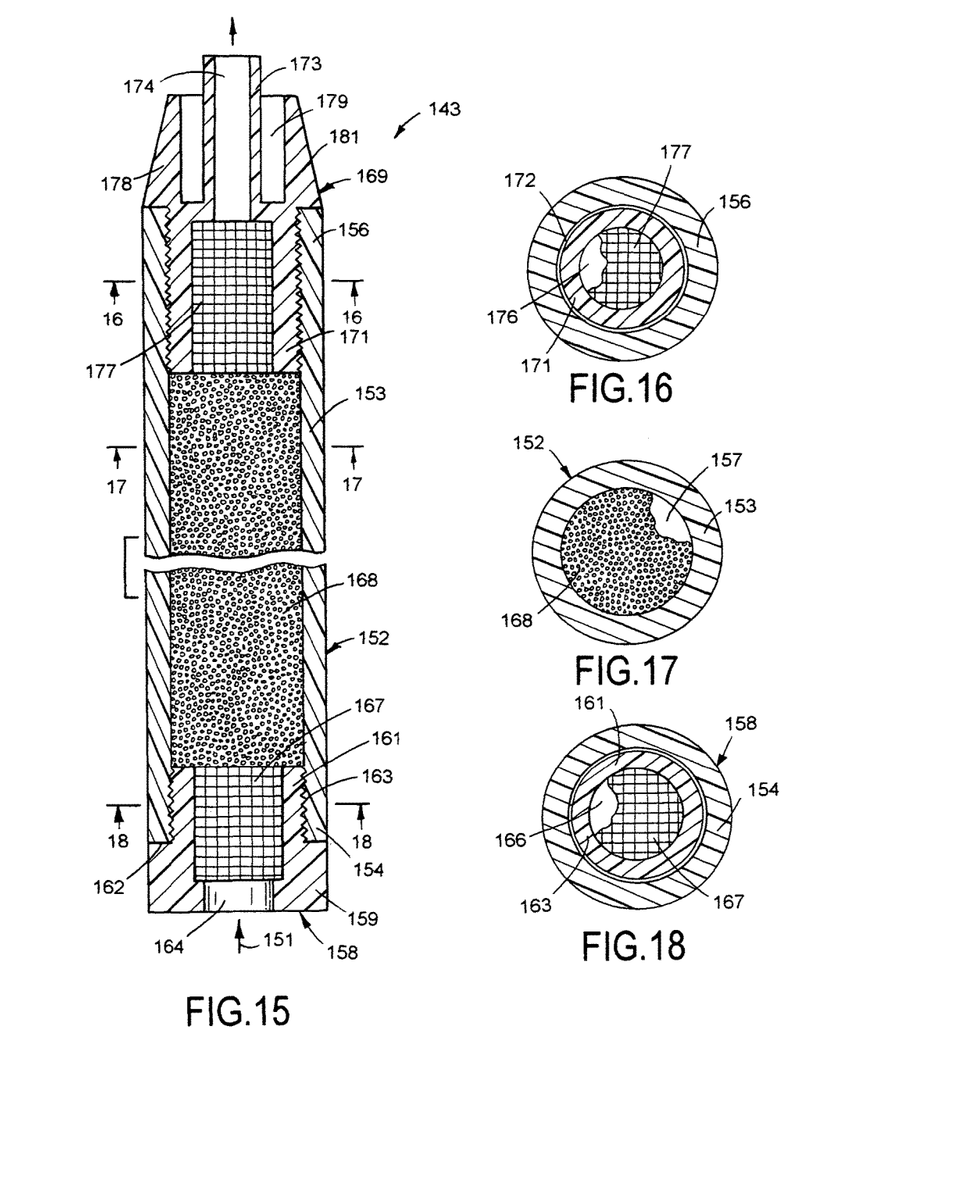
FIG. 15 is a foreshortened sectional view taken along line 15-15 of FIG. 12.
FIG. 16 is a sectional view taken along line 16-16 of FIG. 15.
FIG. 17 is a sectional view taken along line 17-17 of FIG. 15.
FIG. 18 is a sectional view taken along line 18-18 of FIG. 15.

As shown in FIGS. 8, and 9; chamber 57 contains a bed of disinfectant material 68 that has germicidal functions to neutralize and destroy water contaminants including bacteria, viruses and other pathogens. The disinfectant material 68 also supplies a residual disinfectant in the water flowing out of cartridge 43. The residual disinfectant eluted from the disinfectant material 68 neutralizes water contaminants in tube 41, hose 37 and hand piece 38. The materials of tube 41 and hose 37 absorb disinfectant until the inside walls of tube 41 and hose 37 become passivated or saturated with disinfectant to prevent microbial adhesion and biofilm slime in tube 41 and hose 37. The water spray dispensed from hand piece 38 includes the disinfectant which destroys oral flora and reduces the potential cross-infection between dental patients and prevents disease transmission to the patients.

An example of disinfectant material 68 is a resin containing polyiodide, $I_5$, as described by Lambert and Fina in U.S. Pat. No. 4,238,477 and Fina, Lambert and Bridges in U.S. Pat. No. 4,999,190. A continuous release of iodine into the water neutralizes disease causing bacteria, viruses and other pathogens. Iodine is an effective disinfectant for water borne pathogenic bacteria and viruses. An alternative disinfectant material can be an iodinated anionic exchange resin manufactured and sold by MCV Technologies International, Inc. of Belleville, Ill. This resin releases a specific and consistent amount of iodine into the water flowing in chamber 57 to neutralize the microbial contaminates in the water. The disinfectant material 68 can be a resin matrix iodinated with elemental iodine, $I_2$, to a level of 2 to 6 ppm of iodine in water flowing through the resin. The resin contains approximately 46 percent by weight active iodine and 54 percent by weight of inactive ingredients. The effluent iodine removes biofilm from tube 41, hose 37 and hand piece 38 and performs a germicidal function thereon. The disinfectant material 68 can be a silver composition that contains silver and a metal or a silver impregnated activated carbon that maintains sufficient amounts of silver ions in the water to effectively disinfect the water. Examples of silver self-regulating water purifications are disclosed in U.S. Pat. Nos. 5,223,149 and 6,254,894.

A second end member 69 on the outlet end portion 56 of body 52 has a sleeve 71 and tubular nipple 73. Sleeve 71 and end portion 56 have cooperating threads 72 that releasably connect member 69 to body 52. Thread 72 allows end member 69 to be assembled on an removed from body 52. Sleeve 71 has a cavity 76 open to chamber 57 and a passage 74 in nipple 73 to allow water to flow from chamber 57 into the lumen of tube 41. A filter 77 located in cavity 76 prevents disinfectant material 68 from flowing through end member 69 into tube 41. Filter 77 is a cylindrical polypropylene porous member that fills cavity 76 with a tight fit contact with sleeve 71. Filter 77 can extend inwardly into chamber 57. Other types of filters and screens can be used to confine the disinfectant material 68 to chamber 57. An annular outside wall 78 joined to sleeve 71 surrounds nipple 73. Wall 78 spaced from nipple 78 provides an annular pocket 79. Tube 41 telescoped on nipple 73 extends into pocket 79 to connect tube 41 to end member 69 and allow water to flow from cartridge 43 to cap 17 and hand piece 38. Alternative connections, such as a luer connector, can be used to retain tube 41 on nipple 73.

A second embodiment of a cartridge 143, shown in FIGS. 12 to 18, is useable with water dispensing apparatus 10 to disinfect water supplied to dental hand piece 38. Cartridge 143 has the same structures as cartridge 43 with like element having the same reference numbers with the prefix 1. Cartridge 143 has an elongated cylindrical body 152 with first and second end members 158 and 159 releasably connected to opposite end portions 154 and 156 of body 152. First end member 159 has a cylindrical body 159 joined to a sleeve 161. End portion 154 of side wall 153 of body 152 and sleeve 161 have cooperating threads 163 that releasably connect end member 159 to body 152. End member 159 can be removed from body 152 and replaced with another or different end member. End member 159 has an annular shoulder 162 located in engagement with the end of end portion 152 when end member 159 is located on body 152. End member 158 has an opening 164 in communication with a cavity 166 within sleeve 161. A filter 167 disposed in cavity 166 removes particulates from water flowing through filter 167 into chamber 157 located within cylindrical wall 153 of body 152. A bed of disinfectant material 168 located within chamber 157 destroys and neutralizes bacteria, viruses and pathogens in the water flowing in chamber 157. Disinfectant material 168 is the same as disinfectant material 68. Second end member 169 has a sleeve 171 mounted on end portion 156 of body 152. Cooperating threads 172 on end portion 156 and sleeve 171 releasably retain sleeve 171 on body 152. End member 169 has a tubular nipple 173 having a passage 174 open to a cavity 176 within sleeve 171. A filter 177 located in cavity 176 prevents disinfectant material 168 from flowing with water through the filter 177 into passage 174 and hose 37 and hand piece 38. End member 169 has an annular wall 178 located around nipple 173 providing an annular pocket 179 for accommodating a tube connecting cartridge 1443 to cap 17. Annular wall 178, shown in FIGS. 12 and 13, has a plurality of inwardly tapered ribs 181 that facilitate manual turning of end member 169 onto body 152 and the removal of end member 169 from body 152.

Figure 19:
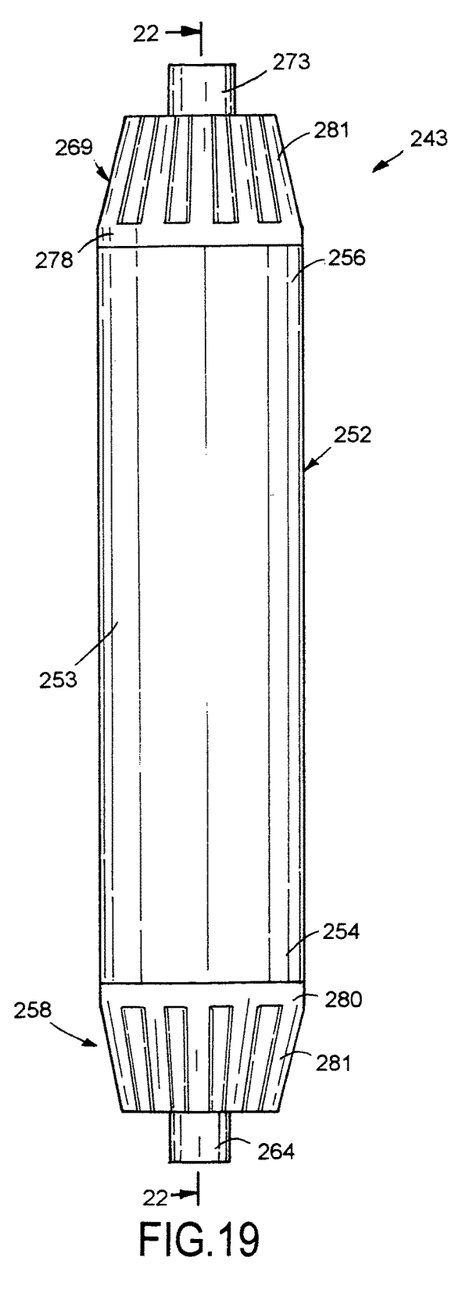
FIG. 19 is an enlarged foreshortened front elevational view of a third embodiment of the water disinfectant cartridge.
Figure 20:
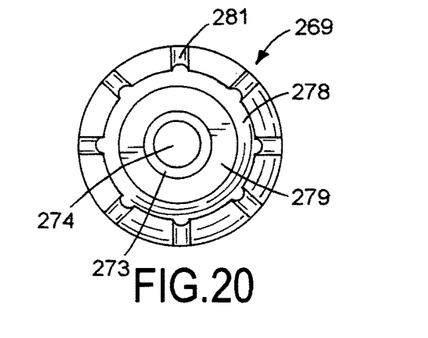
FIG. 20 is a top plan view of FIG. 19.
Figure 21:
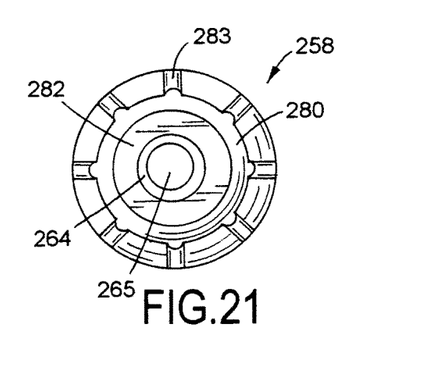
FIG. 21 is a bottom plan view of FIG. 19.
Figure 22:
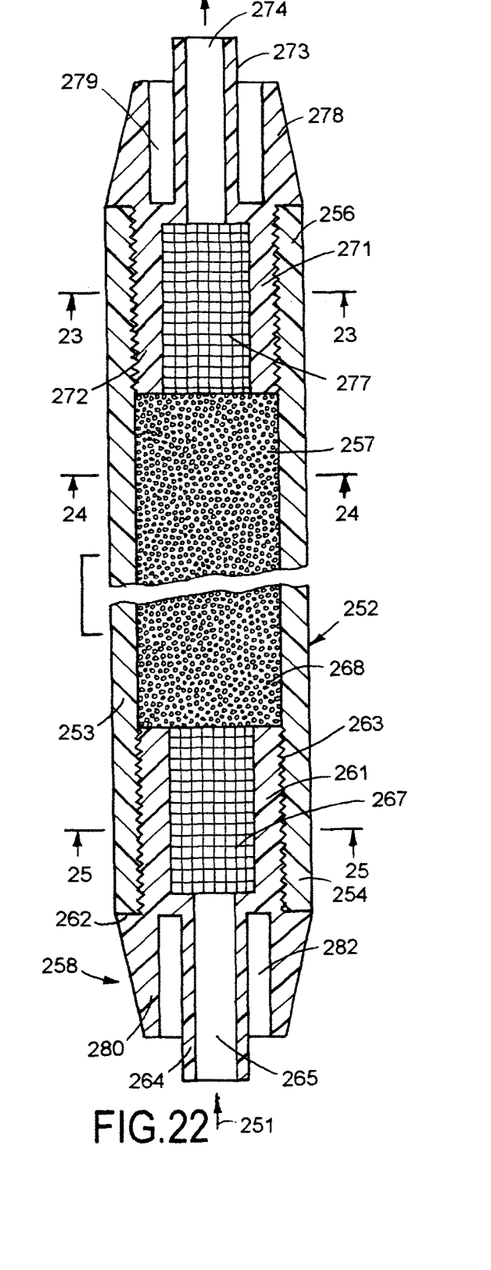
FIG. 22 is a foreshortened sectional view taken along the line 22-22 of FIG. 19.
Figure 23:
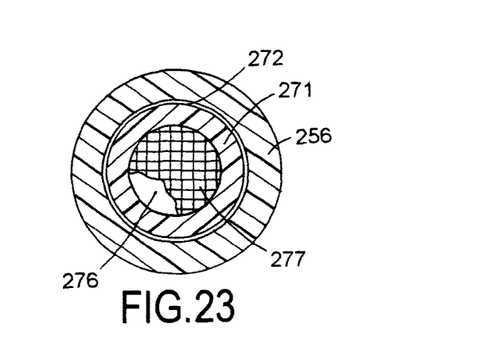
FIG. 23 is a sectional view taken along line 23-23 of FIG. 22.
Figure 24:
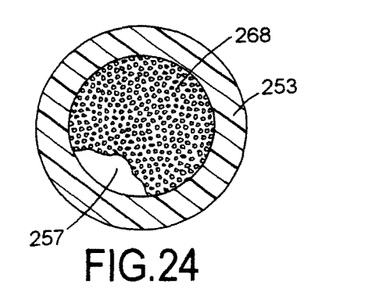
FIG. 24 is a sectional view taken along the line 24-24 of FIG. 22.
Figure 25:
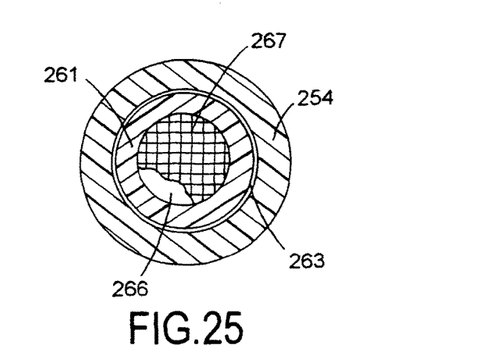
FIG. 25 is a sectional view taken along the line 25-25 of FIG. 22.

A third embodiment of a cartridge 243, shown in FIGS. 19 to 25, is usable with water dispensing apparatus 10 to disinfect water supplied to dental hand piece 38. Cartridge 243 has the same structures and functions as cartridge 43 with the same elements having the same reference numbers with the prefix 2. The first end member 258 has the same structure as second end member 269. This allows the first and second end members 258 and 269 to be selectively connected to tube 41. The cartridge 243 can also be used in water lines to disinfect water. As shown in FIGS. 19, 20 and 21, end members 258 and 269 each have a plurality of tapered ribs 281 and 283 that facilitate manual turning of end members 258 and 269 onto the opposite ends of body 252. End members 258 and 269 have annular pockets 282 and 279 for accommodating tubes or conduits for supplying water to and discharging treated water from cartridge 243 to a remote location. A bed of disinfectant material 268 located in chamber 257 neutralizes bacteria, viruses and pathogens in the water flowing through the disinfectant material 268. Disinfectant material 268 includes the same resins disclosed with regard to disinfectant material 68. These resins are incorporated by reference to identify disinfectant material 268.

Figures 26, 27, 28:
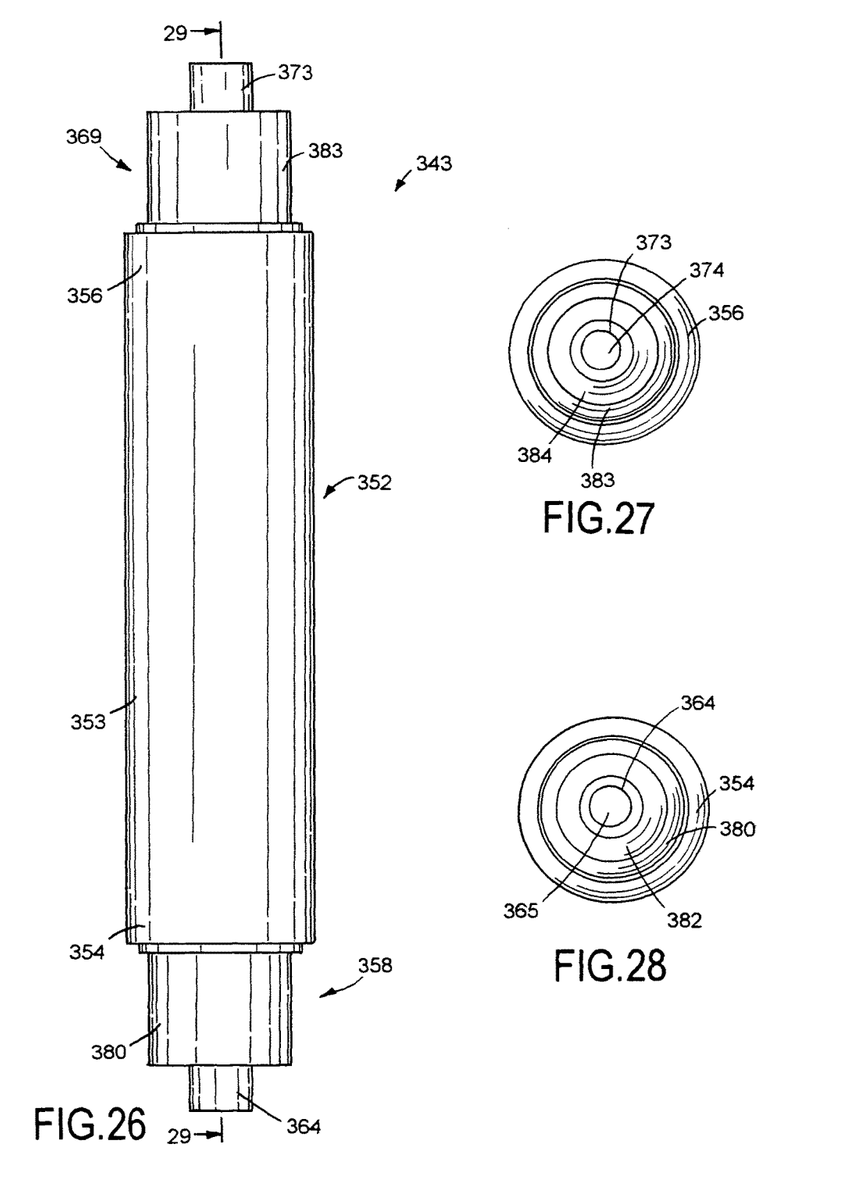
FIG. 26 is an enlarged foreshortened front elevational view of a fourth embodiment of the water disinfectant cartridge.
FIG. 27 is a top plan view of FIG. 26.
FIG. 28 is a bottom plan view of FIG. 26.
Figure 29:
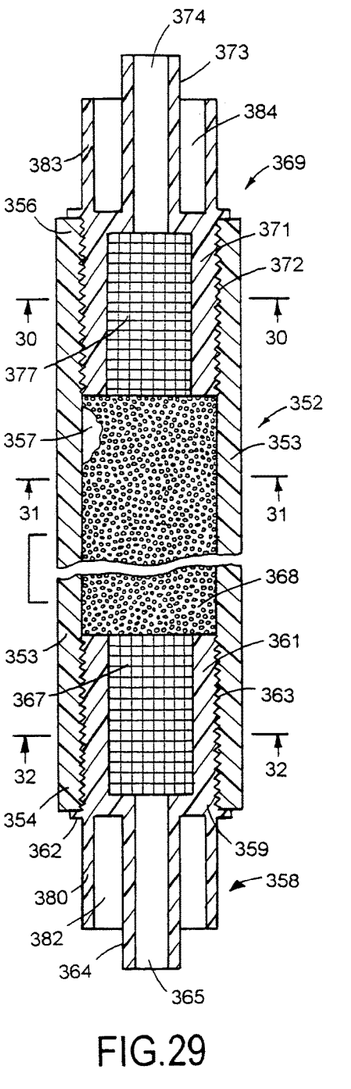
FIG. 29 is a sectional view taken along line 29-29 of FIG. 26.
Figure 30:
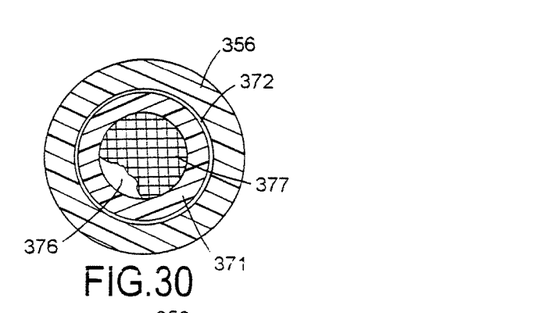
FIG. 30 is a sectional view taken along line-30-30 of FIG. 29.
Figure 31:
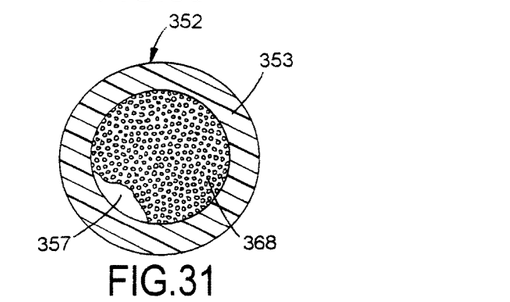
FIG. 31 is a sectional view taken along line 31-31 of FIG. 29.
Figure 32:
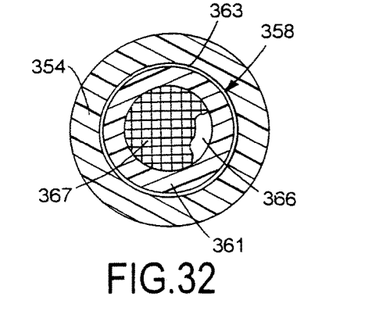
FIG. 32 is a sectional view taken along the line 32-32 of FIG. 29.

A fourth embodiment of a cartridge 343 shown in FIGS. 26 to 32, is usable with a water dispensing apparatus 10 to disinfect water supplied to dental hand piece 38. Cartridge 343 has the same structures and functions as cartridge 43 with the same elements having the same reference numbers with the prefix 3. End members 358 and 369 releasably connected to the opposite ends of tubular body 352 have identical structures that can be connected to tubes or conduits for supplying water to cartridge 343 and allowing water to flow out cartridge 343. Cartridge 343 can be inserted into a water line connecting a dental hand piece to a supply of water. As shown in FIGS. 26 and 29, end members 358 and 369 have tubular nipples 364 and 373 adapted to be inserted into tubes or conduits accommodating water. As shown in FIGS. 29 and 32, end member 358 has a body 359 joined to a sleeve 361, nipple 364 and an annular wall 380. The end portion 352 of wall 353 and sleeve 361 have cooperating threads 363 operable to releasably attach end member 358 on body 352. A filter 367 located in a cavity 366 in sleeve 361 is operable to collect particulates and foreign matter from water flowing through filter 367. End member 369 has the same structures as end member 358. End member 369 has a sleeve 371 and annular wall 383. Sleeve 371 and adjacent end portion of body 352 have cooperating threads 372 that releasably attach sleeve 371 to body 352. A filter 377 located in a cavity 376 in sleeve 371 retains disinfectant material 368 in chamber 357. A bed of disinfected material 368 located in chamber 357 neutralizes bacteria, viruses and pathogens in the water flowing through disinfectant material 368. Disinfectant material 368 includes the same resins disclosed with regard to disinfectant material 68. These resins are incorporated by reference to identify disinfected material 368.

As shown in FIGS. 2 and 8, cartridge 43 containing disinfectant material 68 is installed on cap 17 by connecting tube 41 on nipple 73. Tube 41 telescopes onto nipple 73 and extends into annular pocket 79. Tube 41 has a compression fit on nipple to prevent leakage of water from tube 41. The neck 13 of container 11 is located adjacent sleeve 19 of cap 17. Container 11 is turned about its upright axis whereby threads 26 cooperate to secure container 11 to cap 17. The top annular end of neck 13 engages O-ring 27 to prevent air and water from leaking out of container 11. The water supply unit is activated to discharge water 16 into the internal chamber of container 11. Valve 46 is used to control the amount of water directed into tube 21 and container 11. Air 50 generated by air pump 29 is directed through check valve 31 into tube 32 coupled to cap 17. Cap passage 34 delivers air under pressure to the internal chamber of container 11. Water 16 in internal chamber of container 11 subjected to air pressure is forced into cartridge 43 and out of cartridge 43 to cap 17 and dental instrument 38. Dental instrument has manually operated a water control valve 40 that regulates the flow or spray of water from the operating end of dental instrument 38. Cartridge 43 elutes the disinfectant into water flowing through the disinfectant material and out of the second end member 69 to the dental instrument 38 at a bacteria level of less than 200 cfu. In a typical water treatment dispensing apparatus, cartridge 43 may be used for about 365 days or until the disinfectant, such as iodine, falls below 0.5 ppm. After use, cartridge 43 is removed from container 11. A new container is then attached to cap 17. The water treatment dispensing apparatus is ready for further use.

There has been shown and described several embodiments of water disinfectant cartridges usable with a water treatment dispensing apparatus. Changes in material, structures and disinfectant materials can be made by persons skilled in the art without departing from the invention.

The invention claimed is:

1. A water treatment dispensing apparatus comprising:
 a container having an chamber within for holding water and a neck having a passage open to the chamber,
 a cap releasably mounted on the neck of the container, said cap having first, second and third passages open to the passage in the neck,
 a water supply unit for directing water to the first passage in the cap to supply water to the chamber of the container,
 an air pressure supply device for directing pressurized air to the second passage in the cap and the chamber of the container to subject the water in the chamber of the container to air pressure,
 an air pressure gauge mounted on the cap operable to monitor the pressure of the air in the chamber of the container,
 a cartridge located in the chamber of the container extended into the water in the chamber of the container,
 said cartridge having an elongated tubular body with first and second end portions, the elongated tubular body having a side wall defining an internal chamber,
 a bed of disinfectant material located in the internal chamber of the body of the cartridge for neutralizing bacteria, viruses and pathogens in the water in the internal chamber of the body of the cartridge,
 a first end member mounted on the first end portion of the body,
 said first end member including a first sleeve having a first cavity located within the first end portion of the body the first cavity located within and extending into the internal chamber, and a fifth passage open to the chamber of the container and the first cavity,
 a first filter located in the first cavity of the first sleeve for removing organic and inorganic materials from the water flowing through the first filter from the chamber of the container into the internal chamber of the cartridge, the first filter extending longitudinally in the first cavity, the first filter filling the first cavity of the first sleeve and contacting an inner surface of the first sleeve defining boarders of the first cavity, the first filter positioned to not protrude outside the first cavity, and the first filter having an elongated cylindrical shape,
 a second end member mounted on the second end portion of the body of the cartridge,
 a tubular member connecting the second end member to the cap for carrying water from the second end member to the third passage in the cap,
 said second end member including a second sleeve having a second cavity located within the second end portion of the body, the second cavity extending axially into the internal chamber, and a sixth passage open to the second cavity and the tubular member,
 where the second sleeve and the second end portion of the elongated tubular body have cooperating threads for releasably connecting the second end member to the second end portion of the elongated tubular body of the cartridge;
 a second filter located in the second cavity for preventing the disinfectant material in the internal chamber of the body from moving with water through the second cavity into the tubular member, the second filter extending longitudinally in the second cavity, the second filter filling the second cavity of the second sleeve contacting an inner surface of the second sleeve defining boarders of the second cavity and the second filter positioned to not protrude outside the second cavity; and the second filter having an elongated cylindrical shape a conduit connected to the cap in communication with the third passage in the cap for carrying water from the cap to a selected location, wherein the first and second filter filters do not contact the side wall.

2. The water treatment dispensing apparatus of claim 1 wherein:
the bed of disinfectant material includes a resin containing polyiodide.

3. The water treatment dispensing apparatus of claim 1 wherein:
the bed of disinfectant material includes an iodinated anionic exchange resin.

4. The water treatment dispensing apparatus of claim 1 wherein:
the bed of disinfectant material includes a resin matrix iodinated with elemental iodine.

5. The water treatment dispensing apparatus of claim 1 wherein:
the bed of disinfectant material includes a silver composition.

6. The water treatment dispensing apparatus of claim 1 wherein:
the first sleeve and the first end portion of the body have cooperating threads for releasably connecting the first end member to the first end portion of the body.

7. The water treatment dispensing apparatus of claim 1 wherein:
the second end member includes a nipple having a seventh passage open to the second cavity to allow water to flow out of the second cavity, and
said tubular member being mounted on the nipple to connect the tubular member to the second end member whereby water flows out of the second cavity and through the passage into the tubular member.

8. The water treatment dispensing apparatus of claim 7 wherein:
the second end member includes an annular wall surrounding the nipple, and
said annular wall being is spaced from the nipple to accommodate the tubular member mounted on the nipple.

9. The water treatment dispensing apparatus of claim 1 wherein:
the first end member includes a first nipple having a passage open to the first cavity to allow water to flow from the chamber of the body into the first cavity and through the first filter into the internal chamber of the cartridge, and the second end member includes a second nipple having a passage open to the second cavity to allow water to flow out of the second cavity,
said tubular member being mounted on the second nipple to connect the tubular member to the second end member whereby water flows out of the internal chamber of the body into the tubular member.

10. The water treatment dispensing apparatus of claim 1 including: a dental instrument connected to the conduit whereby water is supplied to the dental instrument.

11. A water treatment dispensing apparatus of claim 1, wherein the first and second filters have a smaller diameter relative to the diameter of the bed of disinfectant material.

12. A water treatment dispensing apparatus of claim 1, wherein the first and second filter have a porosity of 5 microns.

13. A water treatment dispensing apparatus of claim 1, wherein the elongated tubular body of the cartridge has a single chamber.

14. A water treatment dispensing apparatus of claim 1, wherein the elongated tubular body has a single chamber of claim 1, wherein the bed of disinfectant material is continuous.

15. A water treatment dispensing apparatus of claim 1, wherein the first filter includes activated charcoal.

16. A water treatment dispensing apparatus comprising:
a container having a chamber for holding water and a passage open to the chamber,
a housing mounted on the container for closing the passage open to the chamber, an apparatus for supplying water to the housing and the chamber of the container,
an air pressure supply device for directing pressurized air to the housing and chamber of the container to air pressure,
a cartridge located in the chamber of the container, said cartridge having a body with an internal chamber defined by a side wall
a bed of disinfectant material located in the internal chamber of the body of the cartridge for neutralizing bacteria, viruses and pathogens in the water in the internal chamber of the body of the cartridge,
a first end member attached to the body of the cartridge having a second passage open to the chamber of the container and the internal chamber of the body of the cartridge to allow water subjected to air pressure to flow from the chamber of the container to the internal chamber of the body of the cartridge, said first end member including a first sleeve having a first cavity, the first sleeve located within and extending into the internal chamber,
a first filter associated with the first end member operable to remove organic and inorganic materials from the water flowing through the first filter into the internal chamber of the body of the cartridge, the first filter located in the first cavity of the first sleeve, the first filter extending longitudinally in the first cavity, the first filter filling the first cavity of the first sleeve of the first end member and contacting the an inner surface of the first sleeve defining borders of the first cavity, the first filter positioned to not protrude outside the first cavity, and the first filter having an elongated cylindrical shape,
a second end member attached to the body of the cartridge having a third passage open to the internal chamber of the body of the cartridge to allow water to flow out of the internal chamber of the body of the cartridge,
said second end member including a second sleeve having a second cavity located within the second end portion, the second cavity extending axially into the internal chamber of the body of the cartridge, and having an inner surface defining borders of the second cavity,
where the second sleeve and second end portion of the elongated tubular body have cooperating threads for releasably connecting the second end member to the second end portion of the elongated tubular body of the cartridge;
a second filter associated with the second end member operable to prevent disinfectant material in the internal chamber of the body of the cartridge from moving with the water through the second end member, the second filter extending longitudinally in the second cavity, and filling the second end member, the second filter having an elongated cylindrical shape, wherein the first and the second filters have diameters smaller than the bed of disinfectant material located in the internal chamber of the body of the cartridge, a first member connecting the second end member to the housing to allow water to flow from the internal chamber of the body of the cartridge to the housing, and a second member connected to the housing for carrying water from the housing to a selected location, wherein the air pressure in the chamber of the container is sufficient to force the water to flow through the cartridge and the second member to the selected location.

17. The water dispensing apparatus of claim 16 including: an air pressure gauge connected to the housing operable to monitor the pressure of the air in the chamber of the container.

18. The water dispensing apparatus of claim 16 wherein: the bed of disinfectant material includes a resin containing polyiodide.

19. The water dispensing apparatus of claim 16 wherein: the bed of disinfectant material includes an iodinated anionic exchange resin.

20. The water dispensing apparatus of claim 16 wherein: the bed of disinfectant material includes a resin matrix iodinated with elemental iodine.

21. The water dispensing apparatus of claim 16 wherein: the bed of disinfectant material includes a silver composition.

22. The water dispensing apparatus of claim 16 wherein: the first sleeve and the body of the cartridge adjacent the first sleeve includes cooperating threads for releasably connecting the first end member to the body of the cartridge.

23. The water dispensing apparatus of claim 16 wherein: the second end member includes a nipple having a fourth passage open to the internal chamber of the body of this cartridge to allow water to flow out of the internal chamber of the body,
said first member being mounted on the nipple whereby water flows from the nipple into the first member and to the housing.

24. The water dispensing apparatus of claim 23 wherein: the second end member includes an annular wall surrounding the nipple, and said annular wall is spaced from the nipple to accommodate the second member on the nipple.

25. The water dispensing apparatus of claim 16 including: a dental instrument connected to the second member whereby water is supplied to the dental instrument.

26. A cartridge for a water dispensing apparatus comprising:
an elongated tubular body having a side wall, an internal chamber and first and second end portions,
a bed of disinfectant material located in the internal chamber of the body for neutralizing bacteria, viruses and pathogens in the water in the internal chamber of the body, the bed of disinfectant material having a first surface and a second surface,
a first end member mounted on the first end portion of the body,
said first end member including a first sleeve having a first cavity located within the first end portion of the body, the first sleeve located within and extending into the internal chamber and having an inner surface defining boarders of the first cavity, and a first passage open to the interior chamber of the body,
a first filter located in the first cavity of the first sleeve for removing organic and inorganic materials from the water flowing through the first filter into the internal chamber of the body, the first filter not protruding outside the first cavity of the first sleeve, the first filter extending longitudinally in the first cavity, the first filter filling the first cavity of the first sleeve and contacting the inner surface of the first sleeve, the first filter having an elongated cylindrical shape,
a second end member mounted on the second end portion of the body, said second end member including a second sleeve having a second cavity located within the second end portion of the body, the second cavity located within the second end portion of the body, the second cavity extending axially into the internal chamber of the body of the cartridge, and a second passage open to the second cavity, the second sleeve having an inner surface defining borders of the second cavity, and
where the second sleeve and second end portion of the elongated tubular body have cooperating threads for releasably connecting the second end member to the second end portion of the elongated tubular body of the cartridge; and
a second filter located in the second cavity for preventing the disinfectant material in the internal chamber of the body from moving with water through the second cavity and the second passage open to the second cavity, the second filter not protruding outside the second cavity of the second sleeve, the second filter extending longitudinally in the second cavity and contacting the inner surface of the second sleeve, the second filter having an elongated cylindrical shape,
wherein the first and second filter filters do not contact the side wall and the first and the second filters have diameters smaller than the bed of disinfectant material located in the internal chamber of the body.

27. The cartridge of claim 26 wherein: the bed of disinfectant material includes a resin containing polyiodide.

28. The cartridge of claim 26 wherein: the bed of disinfectant material includes an iodinated anionic exchange resin.

29. The cartridge of claim 26 wherein: the bed of disinfectant material includes a resin matrix iodinated with elemental iodine.

30. The water treatment dispensing apparatus of claim 26 wherein: the bed of disinfectant material includes a silver composition.

31. The cartridge of claim 26 wherein:
the first sleeve and the first end portion of the body have cooperating threads for releasably connecting the first end member to the first end portion of the body.

32. The cartridge of claim 26 wherein: the second end member includes a nipple having a third passage open to the second cavity to allow water to flow out of the second cavity.

33. The cartridge of claim 32 wherein: the second end member includes an annular wall surrounding the nipple, and said annular wall is spaced from the nipple to provide an annular pocket between the nipple and an annular wall.

34. The cartridge of claim 26 wherein: the first end member includes a first nipple having a passage open to the first cavity to allow water to flow into the first cavity through the first filter and to the internal chamber of the body, and the second end member includes a second nipple having a passage open to the second cavity to allow water to flow out of the second cavity and through the second filter.

35. A cartridge of claim 26, wherein the second end member includes an annular wall surrounding a nipple, and said annular wall is spaced from the nipple to provide an annular pocket between the nipple and the annular wall.

36. A cartridge of claim 26, wherein the first and second filter have a porosity of 5 microns.

37. A cartridge of claim 26, wherein the elongated tubular body has a single chamber.

38. A cartridge of claim 26, wherein the bed of disinfectant material is continuous.

39. A cartridge of claim 26, wherein the first filter includes activated charcoal.

40. A cartridge for a water dispensing apparatus comprising: a body having an internal chamber defined by a side wall,
   a bed of disinfectant material located in the internal chamber of the body for neutralizing bacteria, viruses and pathogens in the water in the internal chamber of the body, the bed of disinfectant material having a first surface and a second surface,
   a first end member attached to the body,
   said first end member having a first passage to allow water to flow into the internal chamber of the body, said first end member including a first sleeve having a first cavity, the first sleeve located within and extending into the internal chamber;
   a first filter associated with the first end member and internal chamber of the body operable to remove particulates from the water flowing through the first filter into the internal chamber of the body, the first filter located in the first cavity of the first sleeve, the first filter not protruding outside the first cavity of the first end member, the first filter extending longitudinally in the first cavity, the first filter filling the first cavity of the first sleeve and contacting an internal surface of the first sleeve defining the first cavity, the first filter having an elongated cylindrical shape and a porosity of 5 microns,
   a second end member attached to the body,
   said second end member having a second passage open to the internal chamber to allow water to flow out of the internal chamber, said second end member including a second sleeve having a second cavity located within the second end portion of the body, the second cavity extending axially into the internal chamber of the body of the cartridge, and the second sleeve having an inner surface defining borders of the second cavity, and
   where the second sleeve and a second end portion of the body have cooperating threads for releasably connecting the second end member to the second end portion of the body of the cartridge;
   a second filter associated with the second end member and the internal chamber operable to prevent the disinfectant material in the internal chamber of the body from moving out of the internal chamber of the body, the second filter extending longitudinally in the second cavity and contacting an inner surface of the second sleeve defining the second cavity of the second end member, the second filter having an elongated cylindrical shape and a porosity of 5 microns,
   wherein the first and second filters do not contact the side wall, and the first and the second filters have diameters smaller than the bed of disinfectant material located in the internal chamber of the body.

41. The cartridge of claim 40 wherein: the bed of disinfectant material includes a resin containing polyiodide.

42. The cartridge of claim 40 wherein: the bed of disinfectant material includes an iodinated anionic exchange resin.

43. The cartridge of claim 40 wherein: the bed of disinfectant material includes a resin matrix iodinated with elemental iodine.

44. The cartridge of claim 40 wherein: the bed of disinfectant material includes a silver composition.

45. The cartridge of claim 40 wherein:
   the first end member and the body include cooperating threads for releasably connecting the first end member to the body.

46. The cartridge of claim 40 wherein: the second end member includes a nipple having a third passage open to the internal chambers of the body to allow water to flow out of the internal chamber of the body.

47. The cartridge of claim 46 wherein: the second end member includes an annular wall surrounding the nipple, and said annular wall is spaced from the nipple to provide an annular pocket between the nipple and the annular wall.

48. The cartridge of claim 40 wherein: the first end member includes a first nipple having a passage open to the internal chamber of the body to allow water to flow into the internal chamber of the body, and the second end member includes a second nipple to allow water to flow out of the internal chamber of the body.

* * * * *